(12) United States Patent
Bacus

(10) Patent No.: US 8,946,256 B2
(45) Date of Patent: Feb. 3, 2015

(54) COMPOSITIONS AND METHODS FOR TREATMENT OF VITILIGO

(71) Applicant: Sarah Bacus, Hinsdale, IL (US)

(72) Inventor: Sarah Bacus, Hinsdale, IL (US)

(73) Assignee: Biocosmeceuticals, LLC, Hinsdale, IL (US)

( * ) Notice: Subject to any disclaimer, the term of this patent is extended or adjusted under 35 U.S.C. 154(b) by 0 days.

(21) Appl. No.: 13/693,084

(22) Filed: Dec. 4, 2012

(65) Prior Publication Data

US 2013/0101572 A1    Apr. 25, 2013

Related U.S. Application Data

(62) Division of application No. 12/975,275, filed on Dec. 21, 2010.

(60) Provisional application No. 61/288,688, filed on Dec. 21, 2009, provisional application No. 61/315,672, filed on Mar. 19, 2010.

(51) Int. Cl.
```
A61K 31/436    (2006.01)
A61K 38/44     (2006.01)
E01C 23/16     (2006.01)
A61K 31/133    (2006.01)
A61K 31/355    (2006.01)
A61K 38/18     (2006.01)
```

(52) U.S. Cl.
CPC .............. *A61K 38/44* (2013.01); *E01C 23/16* (2013.01); *A61K 31/133* (2013.01); *A61K 31/355* (2013.01); *A61K 31/436* (2013.01); *A61K 38/1825* (2013.01)
USPC ............ 514/291; 514/9.1; 424/94.4; 435/375

(58) Field of Classification Search
USPC .................... 424/94.4; 435/375; 514/9.1, 291
See application file for complete search history.

(56) References Cited

U.S. PATENT DOCUMENTS

| | | | | |
|---|---|---|---|---|
| 4,695,590 | A * | 9/1987 | Lippman | 514/724 |
| 5,286,731 | A * | 2/1994 | Caufield et al. | 514/291 |
| 5,362,735 | A | 11/1994 | Luengo | |
| 5,932,608 | A | 8/1999 | Nguyen et al. | |
| 6,048,886 | A * | 4/2000 | Neigut | 514/412 |
| 6,130,254 | A | 10/2000 | Fisher et al. | |
| 6,936,426 | B2 * | 8/2005 | Smith et al. | 435/7.1 |
| 2002/0168360 | A1 * | 11/2002 | Dingivan et al. | 424/143.1 |
| 2003/0022911 | A1 | 1/2003 | Smith et al. | |
| 2003/0064948 | A1 | 4/2003 | Fahr et al. | |
| 2005/0136111 | A1 | 6/2005 | Glinecke et al. | |
| 2005/0171616 | A1 | 8/2005 | Sung et al. | |
| 2006/0286046 | A1 | 12/2006 | Haber | |
| 2007/0026042 | A1 | 2/2007 | Narayanan | |
| 2007/0027080 | A1 * | 2/2007 | Ramaiah | 514/12 |
| 2008/0107679 | A1 | 5/2008 | Dilallo et al. | |
| 2008/0233183 | A1 | 9/2008 | McCook et al. | |
| 2009/0291066 | A1 | 11/2009 | Pappas et al. | |
| 2009/0291986 | A1 | 11/2009 | Pappas et al. | |

FOREIGN PATENT DOCUMENTS

| | | |
|---|---|---|
| EP | 0 438 856 A2 | 7/1991 |
| EP | 2 123 248 A1 | 11/2009 |
| JP | 2001-261560 A | 9/2001 |
| WO | 99/24036 A1 | 5/1999 |
| WO | 02/13812 A1 | 2/2002 |
| WO | 2004/073622 A2 | 9/2004 |
| WO | 2007/026356 A2 | 3/2007 |
| WO | 2007/099172 A1 | 9/2007 |
| WO | 2008/119070 A1 | 10/2008 |
| WO | 2008/143928 A1 | 11/2008 |
| WO | 2009/118191 A2 | 10/2009 |

OTHER PUBLICATIONS

Bremecker et al. "The role of primary alkanolamines in cosmetic formulation". (1991) International Journal of Cosmetic Science, vol. 13, 235-247.*

Thiele et al. "Vitamin E in human skin: Organ-specific physiology and considerations for its use in dermatology" (2007) Molecular Aspects of Medicine, vol. 28, 646-667.*

Lisa B Travis et al: "Successful Treatment of Vitiligo With 0.1% Tacrolimus Ointment The Cutting Edge: Challenges in Medical and Surgical Therapeutics Report of Cases", Arch Dermatol, May 1, 2003, pp. 571-574, Retrieved from the Internet at <httpp://archderm.jamanetwork.com/data/Journals/DERM/11722/DCE20005.pdf> on Oct. 14, 2014.

Passeron et al: "Physiopathology and genetics of vitiligo", Journal of Autoimmunity, London, GB, vol. 25, Jan. 1, 2005, pp. 63-68.

Extended European Search Report for European Patent Application No. 10840093.8 with a mailing date of Oct. 23, 2014, and Oct. 14, 2104 as the completion date of the search.

Ahmet Korkmaz et al,"Combination of melatonin and a peroxisome proliferator-activated receptor-[gamma] agonist induces apoptosis in a breast cancer cell line", Journal of Pineal Research, vol. 46, No. 1, Jan. 2009, pp. 115-116.

Mao-Qiang et al., Peroxisome-proliferator-activated receptor (PPAR)-gamma activation stimulates keratinocyte differentiation, Invest Dermatol, Aug. 2004;123(2):305-12.

A. Slominski et al., On the Role of Melatonin in Skin Physiology and Pathology, Endocrine, 2005 27(2):137-148.

Extended European Search Report for European Patent Application No. 10 842 740.2 ,with a mailing date of May 8, 2014.

* cited by examiner

*Primary Examiner* — Jon P Weber
*Assistant Examiner* — Teresa E Knight
(74) *Attorney, Agent, or Firm* — Katten Muchin Rosenman

(57) ABSTRACT

Compositions and methods are disclosed for treating vitiligo and promoting the formation of collagen.

16 Claims, 1 Drawing Sheet

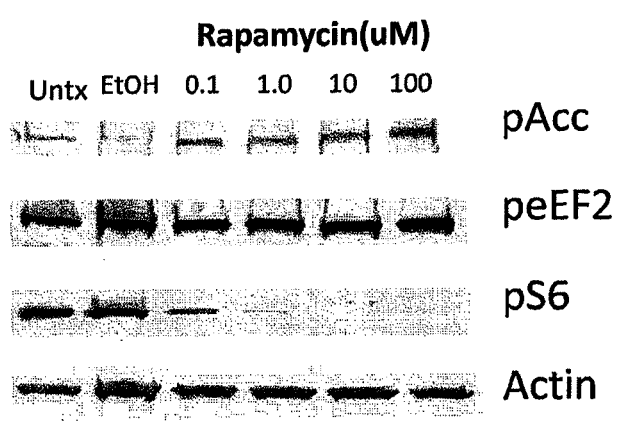

COMPOSITIONS AND METHODS FOR TREATMENT OF VITILIGO

CROSS REFERENCE TO RELATED APPLICATIONS

This application is a divisional of U.S. patent application. Ser. No. 12/975,275, filed Dec. 21, 2010, which claims priority to U.S. Provisional Patent Appln. No. 61/288,688 filed on Dec. 21, 2009, entitled "Compositions and Methods for Treatment of Vitiligo" and U.S. Provisional Patent Appln. No. 61/315,672 filed Mar. 19, 2010, entitled "Formulations for Skin Cream Compositions by Sarah Bacus, all of which are hereby incorporated by reference.

TECHNICAL FIELD

The present invention relates to a novel skin composition that stops progression of vitiligo. The invention further relates to a composition containing a compound functioning to inhibit T-cell killing in the melanocytes. More specifically, the invention relates to a composition containing rapamycin as an active ingredient. In addition, the invention can contain fibroblast growth factor as an active ingredient. The invention further relates to a composition for promoting the formation of collagen in the skin, wherein the composition comprises the aforementioned compound or compounds. The invention also relates to a method of treating related skin signs of aging (hollowing or sagging of skin) through use of the composition.

BACKGROUND

The aging process has multiple effects on the overall thickness and elasticity of the cells which comprise the skin. As skin ages, the amount of collagen produced is decreased and the type of collagen changes. In addition, the elastin in the skin decreases, the melanin granules collect into areas of dark-colored blemishes, the cells of the skin become older and the layers of expired cells increases. There are some remedies available to address these problems. Traditionally, retin-A is used to increase collagen production, decrease elastin loss, decrease production of metalloproteases (which may cause oxidative damage to the skin), disperse melanin granules and exfoliate the layers of dead skin cells from the skin. However, retin-A has some undesirable side effects and requires monitoring of sun exposure while treating skin. There are additional treatments for aging skin such as hydroquinone (bleaches skin and slows melanin production), alpha hydroxy acid (acts similar to retin-A), anti-oxidants (e.g. Cellex-C, Prevage or Revale). There is a continuing need for the development of skin care products that aid in the appearance of younger, more vibrant, healthy looking skin.

Vitiligo is an autoimmune disease presenting with progressive loss of skin pigmentation. Vitiligo is a cutaneous disease in which the melanocytes are destroyed in discrete patches, resulting in lightened areas of variable size and location distributed throughout the skin of the body. Melanocytes are cells located in the stratum basale (bottom layer) of the skin's epidermis. They are also located in the eye, ear, meninges, bones and heart. Melanocytes produce a pigment called melanin, a derivative of the amino acid tyrosine, through the process of melanogenesis. Variations in the activity of melanocytes and the production of melanin is a primary determinant of human skin color. The condition of vitiligo can also affect eye pigmentation and ear function, as melanin is expressed in both the ear and the uveal tract of the eye. The lightened lesions of the skin are immunocompromised and generally have greater susceptibility to the damaging effects of the sun, premature aging and possible cancer of the skin. The disease strikes about 1% of the world population, generally during teenage years. The progressive loss of melanocytes from depigmenting vitiligo skin is accompanied by cellular infiltrates containing T lymphocytes. Infiltrating cytotoxic T cells with high affinity T cell receptors have likely escaped clonal deletion in the thymus, allowing such T cells to enter the circulation. It is thought that through the expression of cutaneous lymphocyte antigen, these T cells home to the skin where they express type 1-cytokine profiles and mediate melanocyte apoptosis via the granzyme/perforin pathway. As this condition affects the skin and is readily visible to the public eye, there are many psychological and social problems that can result. Hence, there is a great need for continuing development of treatments that can be used to minimize the visible consequences of a condition such as vitiligo, as well as other conditions which manifest themselves as discolorations of the skin (aging spots, liver spots, etc.).

SUMMARY OF THE INVENTION

Compositions are disclosed for cosmeceuticals that aid in the retardation of the progression of vitiligo. Methods for preparing cosmeceutical compositions for treating vitiligo are also disclosed. More specifically, the methods herein disclose the use of rapamycin for preventing the progression of vitiligo and the use of rapamycin and fibroblast growth factor for promoting collagen formation. In addition, methods for preparing cosmeceutical compositions resulting in a promotion of collagen are also disclosed. More specifically, the methods herein disclose the use of rapamycin and fibroblast growth factor for promoting collagen formation.

In one aspect of the invention, the composition contains rapamycin in a cosmeceutically acceptable medium/vehicle that functions to reduce T-cell degradation of melanocytes and lessen the visual signs of vitiligo.

In another aspect of the invention, the composition contains additional ingredients, such as fibroblast growth factor to aid in collagen formation.

In yet another aspect of the invention, the composition contains vitamin E.

In additional aspects of the invention, the composition contains tromethamine, glutathione peroxidase, and catalase.

In one embodiment, the invention is administered topically.

In another embodiment, the compositions is formulated as a leave-on product.

In yet another aspect of the invention, the composition contains about 0.001 to 0.5% by weight rapamycin.

In another embodiment, the composition contains about 0.1 to 0.2% by weight rapamycin.

In yet another embodiment, the composition contains about 0.15% by weight rapamycin.

In an additional embodiment the composition is used in a method of treating vitiligo involving topical administration of one of the rapamycin compositions disclosed.

In another embodiment, the composition is used in a method of promoting collagen production involving topical administration of one of the rapamycin compositions disclosed Another embodiment is a method of inhibiting T cells in melanocytes by administering an about 0.1 uM to 100 uM of rapamycin composition to the cells.

DESCRIPTION OF THE DRAWINGS

These and other advantages of the present invention will be readily understood with reference to the following specifications and attached drawings wherein:

FIG. 1. Western blot of protein expression in Human Hepatocarcinoma, HH, (T-cell lymphoma) cells treated with increasing doses of rapamycin (0.1-100 uM).

DETAILED DESCRIPTION

Preferred embodiments of the present invention will be described herein below with reference to the accompanying drawings. In the following description, well-known functions or constructions are not In one aspect, the present invention is based on the discovery that drugs, such as rapamycin, actively inhibit T-cells and inhibit the process of T-cell maturation in the melanocytes. It has been further discovered that the use of rapamycin in cosmeceutical medium is an effective topical treatment for vitiligo. The response of vitiligo skin cells to treatment with rapamycin over a course of treatment (twice a day application of 2.5 uM cosmeceutical rapamycin composition) has shown response via reduction of the discoloration and reduction in the progression of the disease. In another aspect of the present invention, the use of rapamycin and fibroblast growth factor (FGF) promotes the production of collagen and reduces the visible effects of aging.

Rapamycin (also called sirolimus) inhibits the response to interleukin-2 (IL-2) and blocks activation of T- and B-cells. Rapamycin binds to the cytosolic protein FK-binding protein 12 (FKBPI2) and inhibits the mammalian target of rapamycin (mTOR) pathway by directly binding the mTOR Complex 1 (mTORC1).

The treatment of vitiligo and the production of collagen with a rapamycin composition, an FGF composition or a rapamycin and FGF composition of the present invention has many desired effects in management of skin and skin disorders, including anti-ageing, antiwrinkle and/or an anti-cellulite effects, minimizing the appearance of wrinkles, blemishes, skin lines, oily skin, acne, dry skin, xerosis, ichthyosis, dandruff, brownish spots, keratoses, melasma, lentigines, age spots, dark circles around eyes, skin pigmentation, topical inflammation, liver spots, pigmented spots, wrinkles, blemishes, skin lines, oily skin, acne, warts, eczema, pruritic skin, psoriasis, inflammatory dermatoses, disturbed keratinization, dandruff, bacterial infection, fungal infection, wound healing, body odor, and skin changes associated with aging.

Cosmetically Acceptable Vehicle

The composition according to the invention also comprises a dermatologically/cosmetically acceptable vehicle to act as a diluent, dispersant or carrier for the rapamycin. The vehicle can comprise materials commonly employed in skin care products such as water, liquid or solid emollients, silicone oils, emulsifiers, solvents, humectants, thickeners, powders, propellants and the like. Other agents which can be employed in the present application as the dermatologically acceptable vehicle include fibroblast growth factor (FGF), tromethamine, glutathione peroxides, catalase, sphingoid and phospholipid derivatives, antioxidants and vitamins, antiinflammatories, botanical agents, moisturizing agents, skin whitening agents, peptides, caffeine and sunscreens and UV absorbers. Examples of vehicle ingredients include water, glycerin, hydrogenated polyisobutene, cetearyl alcohol, ceteareth-20, macadamia integrifoliaseed oil (macademia nut oil), dimethicone, tocopheryl acetate, stearoxytrimethylsilane, stearyl alcohol, panthenol, farnesol, benzyl alcohol, phenoxyethanol, acrylates/C10-30 alkyl acrylate crosspolymer, sodium hydroxide, citric acid for lotions or water, petrolatum, glyceryl polymethacrylate, dicaprylyl ether, glycerin, dimethicone, glyceryl stearate, cetyl alcohol, prunus amygdalus dulcis (sweet almond) oil, PEG-30 glyceryl stearate, tocopheryl acetate, benzyl alcohol, phenoxyethanol, sodium hydroxide, acrylates/C10-30 alkyl acrylate crosspolymer, disodium EDT A, propylene glycol for creams. A preferred vehicle is Cetaphil®. Examples of some of the agents that can be added to the vehicle include: sphingoid and phospholipid derivatives (e.g. ceramides, phytosphingosine, sphingosine, pseudoceramides, phospholipids, lysophospholipids); antioxidants and vitamins (e.g. tocopherol and derivatives, ascorbic acid and derivatives, niacinamide and derivatives, vitamin complexes, alpha-lipoic acid, retinol and derivatives, panthenol); antiinflammatories (e.g. bisabolol, allantoin, phytantriol, Coenzyme Q10, Idebenone); botanical agents such as polyphenolics, flavonoids or isoflavones; moisturizing agents (e.g. amino acids, hyaluronic acid and derivatives, creatine and derivatives, trimethylglycine, myo-inositol, pyroglutamatic acid and derivatives, taurine, guanidine and derivatives and hydroxy acids); skin whitening agents (e.g. kojic acid, arbutin, vitamin C and derivatives, hydroquinone); peptides, modified peptides, protein hydrolysates.

FORMULATION TABLE

| | Rapamycin (FW = 914.17) 200 mg in 500 ul DMSO (0.4 mg/ul) | | | | |
|---|---|---|---|---|---|
| Desired Conc. | Desired Percent Conc. (% w/v) | Total Volume/Mass Desired | Amount Active Ingredient | Amount Active Ingredient (mgs) | Amount of Stock |
| 0.005 | 0.5 | 15 gms | 0.075 gms | 75 mgs | 187.5 uls of the 0.4 |
| 0.001 | 0.1 | 15 gms | 0.015 gms | 15 mgs | 37.5 uls of the 0.4 |
| 0.0005 | 0.05 | 15 gms | 0.0075 gms | 7.5 mgs | 18.75 uls of the 0.4 |
| 0.0001 | 0.01 | 15 gms | 0.0015 gms | 1.5 mgs | 3.75 uls of the 0.4 |
| 0.00005 | 0.005 | 15 gms | 0.00075 gms | 0.75 mgs | 1.875 uls of the 0.4 |

The cosmeceutically effective amount of rapamycin that is used in the cosmeceutically acceptable composition has a concentration of about 0.5% to 0.00001% rapamycin preferably from about 0.5% to 0.1%. The cosmeceutically effective amount of rapamycin is partially dependent on the cells or the individual being treated and higher concentrations may be necessary to achieve desired results, in addition higher concentrations may result in increased side effects. The Fonnulation Table shows exemplary calculations for producing products of 0.01% and 0.005% rapamycin, similar calculations can be used to produce a cosmeceutically acceptable composition at the desired concentration. For example some preferred amounts of ingredients that may be used in any combination in the composition with 10 gms of vehicle are indicated: addition of about 15 mgs of rapamycin is preferred (about 0.15% by weight), addition of about 0.5 ugm to about 1.5 ugm of fibroblast growth factor is preferred (about 0.00005% to 0.00015% by weight), addition of about 0.5 gms of tromethamine is preferred (about 0.5% by weight), addition of about 30 mgs of glutathione peroxides is preferred (about 0.3% by weight), addition of about 30 mgs of catalase is preferred (about 0.3% by weight), and addition of about 500 mgs of vitamin E is preferred (about 0.5% by weight).

The dermatologically acceptable vehicle will usually form from about 80% to about 99.999%, preferably from about 95% to about 99.985% and most preferably about 99.985% by weight of the composition, and can, in the absence of other cosmetic adjuncts, form the balance of the composition. In a preferred embodiment, the rapamycin is maintained at a concentration of about 0.15% by weight in a cosmeceutically acceptable medium. In another preferred embodiment, the fibroblast growth factor is maintained at a therapeutically effective concentration of about 0.000015% to about 0.00005% in a cosmeceutically acceptable medium. In another embodiment, the rapamycin and FGF together, comprise about 0.15% by weight in a cosmeceutically acceptable medium.

The skin care formulation can be an aqueous solution, a water-in-oil (w/o) emulsion, an oil-in-water (o/w) emulsion, a dispersion of lipids, an aqueous, water-alcohol, oil or oil-alcohol gel, a solid stick, a wet-wipe or an aerosol. If the dermatologically acceptable vehicle itself is an (w/o) or (o/w) emulsion, it can contain 5 to 50% of an oilphase and 47 to 94.95% water, with respect to the weight of the whole formulation.

Product Preparation, Form, Use and Packaging

To prepare the topical composition according to the present invention, the usual manner for preparing skin care products may be employed. The active components are generally incorporated in a dermatologically acceptable carrier in conventional manner. The active components can suitably be dissolved or dispersed in a portion of the water or another solvent or liquid to be incorporated in the composition. The preferred compositions are oil-in-water or water-in-oil emulsions.

The composition may be in the form of conventional skincare products such as a cream, gel or lotion or the like. The composition can also be in the form of a so-called "rinse-off" product, e.g., a bath or shower gel, possibly containing a delivery system for the actives to promote adherence to the skin during rinsing. Most preferably, the product is a "leave-on" product; a product to be applied to the skin without a deliberate rinsing step soon after its application to the skin.

The composition may be packaged in any suitable manner such as in a jar, a bottle, tube, roll-ball, or the like, in the conventional manner.

The active ingredients described in the present invention may be applied one or more times daily to the portion of skin requiring treatment. The improvement in skin appearance will usually become visible after two weeks of treatment, depending on the status of the initial skin condition, the concentration of the active components used in the composition, the volume of composition used and the frequency of application.

In one embodiment, a small quantity, about 0.25 ml, of the composition is applied to the skin from a suitable container or applicator and spread over and/or rubbed into the skin using the hands or fingers or a suitable device. The composition is formulated as a "leave-on" product and does not require any gloves or special applicators for effective use. Once applied to the skin in the affected area, the composition will begin to elicit the desired effects for treating vitiligo and promoting collagen production.

EXAMPLE 1

As shown in FIG. 1, Human Hepatocarcinoma, HH, cells were treated with increasing doses of rapamycin (0.1-100 uM) and the protein expression profile was analyzed by Western blot. The rapamycin treatment resulted in increased expression of pAcc (phosphorylated acetyl-CoA carboxylase), slightly increased expression of peEF2 (phosphorylated eukaryotic elongation factor 2) and decreased expression of pS6 (phosphorylated ribosomal protein S6). The expression levels of Actin are maintained and serve as a loading control. The increased expression of pAcc and peEF2, and the decreased expression of pS6 illustrate an inhibition of T-cells.

EXAMPLE 2

Vitiligostop

Natural sources of anti fungal agents help to stop the rejection of melanin producing cells which causes the depigmentation of the skin. Vitilogstop is not a cure, but provides a noticeable diminishment of discoloration and enlargement of vitiligo spots usually after three months. Combined with other active ingredients, stimulation of new melanin occurs over time. Apply twice a day on affected sites. The cream may oxidize and darken with time but will remain effective throughout use.

| Vitilgostop | Amount per 10 gms |
|---|---|
| Rapamycin | 15 milligrams |
| Fibroblast Growth Factor 2 | 1.5 micrograms |
| Tromethamine | 0.5% |
| Glutathaion Peroxides | 30 milligrams |
| Catalase | 30 milligrams |
| Vitamin E | 500 milligrams |
| Vehicle | 10 grams |

FORMULATION EXAMPLE

[00411 A 0.4 mg/ul Rapamycin composition is made in DMSO as a stock solution, from which an aliquot of 187.5 uls of the stock solution is added to 200 gms of lotion or cosmeceutically acceptable medium and mixed thoroughly. An FGF composition is made following a similar protocol for a cosmeceutically acceptable medium and mixed thoroughly. Additional concentrations can be made from a concentrated stock solution by methods known to one of ordinary skill in the art. The cosmeceutical formulation (lotion) can be stored at ambient temperature for topical use on those areas of the skin wherein additional lipid production is desired.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

All U.S. and foreign patent documents, all articles, brochures, and all other published documents discussed above are hereby incorporated by reference into the Detailed Description of the Preferred Embodiment.

What is claimed is:

1. A method of treating vitiligo comprising topically administering to an affected area of a subject in need thereof a composition comprising a cosmeceutically acceptable medium and about 0.001 to about 0.1 weight percent rapamycin to treat the subject.

2. The method according to claim 1, wherein the composition further comprises fibroblast growth factor.

3. The method according to claim 2, wherein the composition comprises from about 0.000015 to about 0.00005 weight percent fibroblast growth factor.

4. The method according to claim 1, wherein the composition further comprises vitamin E.

5. The method according to claim 4, wherein the composition comprises about 0.5 weight percent vitamin E.

6. A method according to claim 1, wherein the composition further comprises tromethamine.

7. A method according to claim 6, wherein the composition comprises about 0.5 weight percent tromethamine.

8. A method according to claim 1, wherein the composition further comprises glutathione peroxidase.

9. A method according to claim 8, wherein the composition comprises about 0.3 weight percent glutathione peroxidase.

10. A method according to claim 1, wherein the composition further comprises catalase.

11. A method according to claim 10, wherein the composition comprises about 0.3 weight percent catalase.

12. A method according to claim 1, wherein the composition is a leave-on product.

13. The method according to claim 1, wherein the subject is administered the composition twice daily.

14. The method according to claim 1, wherein the subject is administered about 0.25 mL of the composition twice daily.

15. The method according to claim 1, wherein the subject is administered about 0.35 mL of the composition twice daily.

16. A method of treating vitiligo comprising topically administering to an affected area of a subject in need thereof a composition comprising:
- a cosmeceutically acceptable medium;
- about 0.001 to about 0.1 weight percent rapamycin;
- about 0.000015 to about 0.00005 weight percent fibroblast growth factor;
- about 0.5 weight percent vitamin E;
- about 0.5 weight percent tromethamine;
- about 0.3 weight percent gluthione peroxidase; and
- about 0.3 weight percent catalase.

* * * * *